United States Patent [19]
Zhang et al.

[11] Patent Number: 5,846,718
[45] Date of Patent: Dec. 8, 1998

[54] IDENTIFICATION OF PYRAZINAMIDE-RESISTANT MYCOBACTERIA AND METHODS FOR TREATING MYCOBACTERIAL INFECTIONS

[75] Inventors: Ying Zhang, Baltimore; Angelo Scorpio, Columbia, both of Md.

[73] Assignee: The Johns Hopkins University, Baltimore, Md.

[21] Appl. No.: 655,821

[22] Filed: May 31, 1996

[51] Int. Cl.$^6$ ..................................................... C07H 21/04
[52] U.S. Cl. ........................... 435/6; 536/22.1; 536/23.2; 536/23.7; 536/24.3
[58] Field of Search ................... 536/23.2, 23.7, 536/24.3, 22.1; 435/6

[56] References Cited

PUBLICATIONS

R.M. McCune, Jr., et al., "The Fate of Mycobacterium Tuberculosis in Mouse Tissues as Determined by the Microbial Enumeration Technique", J. Exp. Med. (1956), vol. 104, 763–802.

B.R. Bloom et al., "Tuberculosis: Commentary on a Reemergent Killer", Science (1992), vol. 257, 1055–1064.

K. Konno et al., "Pyrazinamide Susceptibility and Amidase Activity of Tubercle Bacilli", Am. Rev. Respir. Dis., Mar. 1967, vol. 95, 461–469.

M. Orita et al., "Rapid and Sensitive Detection of Point Mutations and DNA Polymorphisms Using the Polymerase Chain Reaction", Genomics, 1989, 5:874–879.

Y. Zhang et al., "Alterations in the Superoxide Dismutase Gene of an Isoniazid–Resistant Strain of Mycobacterium Tuberculosis", Infect. Immun., May 1992, vol. 60, 2160–2165.

P.G. Jerlstrom et al., "Structure and Expression in *Escherichia coli* K–12 of the L–asparaginase I–encoding ansA Gene and its Flanking Regions", Gene, 1989, vol. 78, 37–46.

J.W. Foster et al., "Pyridine Nucleotide Cycle of *Salmoella typhimurium*:Isolation and Characterization of pncA, pncB, and pncC Mutants and Utilization...", J. Bacteriol., Mar. 1979, vol. 137, 1165–1175.

R.K. Saiki et al., "Primer–Directed Enzymatic Amplification of DNA with a Thermostable DNA Polymerase", Science, Jan. 1988, vol. 239, 487–491.

L.G. Wayne, "Simple Pyrazinamidase and Urease Tests for Routine Identification of Mycobacteria", Am. Rev. Respir. Dis., Jan. 1974, vol. 109, 147–151.

W. McDermott, "Activation of Pyrazinamide and Nicotinamide in Acidic Environments in Vitro", Am. Rev. Tuberc., Jul.–Dec. 1954, vol. 70, 748–754.

Scorpio et al., "Mutations in pncA, a gene encoding pyrazinamidase/nicotinamidase, cause resistance to the antituberculous drug pyrazinamide in tubercle bacillus", *Nature*, vol. 2, No. 6, Jun. 1996.

*Primary Examiner*—Kenneth R. Horlick
*Assistant Examiner*—Joyce Timy
*Attorney, Agent, or Firm*—Fish & Richardson P.C.

[57] ABSTRACT

Disclosed are methods, probes, primers and kits for identifying pyrazinamide-resistant mycobacteria. These methods can be used to distinguish *M. bovis* from *M. tuberculosis*, as well as to identify additional pyrazinamide-resistant mycobacteria. Also disclosed are methods for treating mycobacterial infections by expressing a pncA gene in mycobacteria that infect a mammal, and treating the mammal with pyrazinamide. The invention derives from the discovery of that the molecular basis for pyrazinamide resistance is an alteration in the pncA gene of mycobacteria. The detection of such an alteration is an indicator of PZA-resistant mycobacteria.

13 Claims, 5 Drawing Sheets

```
1/1
ATG CGG GCG TTG ATC ATC GTC GAC GTG CAG AAC GAC TTC TGC GAG GGT GGC TCG CTG GCG
Mat arg ala leu ile ile val asp val gln asn asp phe cys glu gly gyl ser leu ala
 61/21                              31/11
GTA ACC GGC GGC GCC GCG CTG GCC CGC GCC ATC AGC GAC TAC CTG GCC GAA GCG GCG GAC
Val thr gly gly ala ala leu ala arg ala ile ser asp tyr leu ala glu ala ala asp
121/41                              91/31
TAC CAT CAC GTC GTG GCA ACC AAG GAC TTC CAC ATC GAC CCG GGT GAC CAC TTC TCC GGC
Tyr his his val val ala thr lys asp phe his ile asp pro gly asp his phe ser gly
181/61                              151/51
ACA CCG GAC TAT TCC TCG TCG TGG CCA CCG CAT TGC GTC AGC GGT ACT CCC GGC GCG GAC
Thr pro asp tyr ser ser ser trp pro pro his cys val ser hyl thr pro hly ala asp
241/81                              211/71
TTC CAT CCC AGT CTG GAC ACG TCG GCA ATC GAG GCG GTG TTC TAC AAG GGT GCC TAC ACC
Phe his pro ser leu asp thr ser ala ile glu ala val phe tyr lys gly ala tyr thr
301/101                             271/91
GGA GCG TAC AGC GGC GTC GAA GGA GTC GAC GAG AAC GGC ACG CCA CTG AAT GGT CTG CTG
Gly ala tyr ser gly phe glu gly val asp glu asn gly thr pro leu leu asn trp leu
361/121                             331/111
CGG CAA CGC GGC GTC GAT GAG GTC GAT GTG GTC GGT ATT GCC ACC GAT CAT TGT GTG CGC
Arg gln arg gly val asp glu val asp val val gly ile ala thr asp his cys val arg
421/141                             391/131
CAG ACG GCC GAG GAC GCG GTA CGC AAT GCC TTG GCC ACC AGG GTG CTG GTG GAC CTG ACA
Gln thr ala glu asp ala val arg asn gly leu ala thr arg val leu val asp leu thr
481/161                             451/151
GCG GGT GTG TCG GCC GTC GAT ACC ACC GTC GCC GCG CTG GAG GAG ATG CGC ACC GCC GTC
ala gly val ser ala asp thr thr val ala ala leu glu glu met arg thr ala ser val
541/181                             511/171
GAG TTG GTT TGC AGC TCC TGA
Glu leu val cys ser ser OPA
```

FIG. 1

P: Primer. *pncA* : *M. tuberculosis* pyrazinamidase gene

FIG. 2

FIG. 3A

```
M. tb          MRALIIVDVQNDFCEGGSLAVTGGAALARAISDYLAE--AADYHHVVATKDFHIDPGD
               ::: :::::::::: ::::  :::::: :
E. coli  MPPRALLLVDLQNDFCAGGALAVPEGDS-TVDVANRLIDWCQSRGEAVIASQDWHPANHG M. tb    HFS---GTPDYSSS------------WPPHCVSGIPGADFHPSLDTSAIEAVFYKG--AYTGA
         ::  :    ::::                :: ::: ::: ::: ::: :::  :  :: ::
E. coli  SFASQHGVEPYTPGQLDGLPQTFWPDHCVQNSEGAQLHPLLHQKAIAAVFHKGENPLVDS M. tb    YSG-FEGVDENGTPLLNWLRQRGVDEVDVVGIATDHCVRQTAEDAVRNGLATRVLVDLTA
         :::  :::  :::   :: :: ::: : :::   :::::: :::  :::::::::::
E. coli  YSAFFDNGRRQKTSLDDWLRDHEIDELIVHGLATDYCVKFTVLDALQLGYKVNVITDGCR M. tb    GVS--ADTTVAALEEMRTASVELVCSS
         :::    :::::
E. coli  GVNIQPQDSAHAFMEMSAAGATLYTLADWEETQG
```

IDENTIFICATION OF PYRAZINAMIDE-RESISTANT MYCOBACTERIA AND METHODS FOR TREATING MYCOBACTERIAL INFECTIONS

FIELD OF THE INVENTION

This invention relates to methods and nucleic acids for identifying pyrazinamide-resistant mycobacteria, including *M. bovis,* and for treating infections with pyrazinamide-resistant mycobacteria.

BACKGROUND OF THE INVENTION

Tuberculosis in humans and other mammals is caused by members of the *M. tuberculosis* complex, which includes *M. tuberculosis, M. bovis, M. africanum,* and *M. microti. M. bovis* and *M. tuberculosis* are closely related, and share more than 99% sequence identity. Although *M. bovis* is the primary cause of tuberculosis in cattle, it is transmissible to humans, where it can cause tuberculosis.

Conventional methods for treating tuberculosis include administration of drugs such as pyrazinamide, isoniazid (INH), rifampicin, streptomycin, and ethambutol. Pyrazinamide (PZA) is particularly useful because it kills certain semi-dormant bacteria that are not affected by other anti-tuberculosis drugs (McCune et al., 1956, J. Exp. Med. 104: 763–802; Heifets et al., 1992, Am. Rev. Respir. Dis. 145: 1223–1225). Thus, inclusion of PZA with INH and rifampicin considerably shortens the typical treatment period from 12–18 months to 6 months, and the three drugs together form the basis of the standard short course chemotherapy (McCune et al., J. Exp. Med. 104, 763–802 (1956); Mitchison, D. S., Tubercle 66, 219–225 (1985)).

Drug-resistant mycobacteria pose a considerable threat to the control of tuberculosis. Indeed, multidrug-resistant (MDR) strains of *M. tuberculosis* have caused several fatal outbreaks in both HIV-positive and HIV-negative individuals (Centers for Disease Control, Florida and New York, 1988–1991, Mortal, Morbid, Weekly Rep. 40, 585–591 (1991); Bloom, et al., Science 257, 1055–1064 (1992)). Strains of *M. bovis* are naturally resistant to PZA, and several strains of *M. tuberculosis* are known to have acquired PZA resistance. Examples of acquired PZA-resistant strains include PZA-R (ATCC 35828) and the clinical isolate M36470, M3S169, F36946, and Vertullo. Because PZA is a commonly used anti-tuberculosis drug, the existence of PZA-resistant strains has complicated efforts to combat tuberculosis infections. Thus, it is important to determine whether the infecting mycobacterium is *M. bovis* or a PZA-susceptible variant of *M. tuberculosis* in order to know whether PZA-based therapy is feasible. Yet, prior to the work described below, the molecular basis of pyrazinamide (PZA) resistance remained unknown. The traditional methods for identifying PZA-resistant mycobacteria, such as *M. bovis,* typically involve time-consuming biochemical assays, which require 2–8 weeks to perform.

SUMMARY OF THE INVENTION

The present invention is based on the discovery of the molecular basis for PZA-resistance in mycobacteria such as *M. bovis.* PZA resistance is conferred by an alteration(s) in the pncA gene of both naturally PZA-resistant mycobacteria and acquired PZA-resistant strains of mycobacteria. The altered pncA genes of PZA-resistant mycobacteria fail to encode functional pyrazinamidase polypeptides.

Accordingly, the invention provides methods, primers, probes, and kits useful for identifying mycobacteria that are resistant to PZA due to alterations in the pncA gene. Also included within the invention are nucleic acids encoding altered PZase polypeptides that confer PZA resistance and wild-type *M. tuberculosis* PZase polypeptide. A substantially purified wild-type *M. tuberculosis* PZase polypeptide and substantially purified altered PZase polypeptides that confer PZA resistance, and antibodies that specifically bind such polypeptides, also are included in the invention. The identification of PZA-resistant mycobacteria is clinically useful for directing the treatment of tuberculosis patients. In addition, conventional biochemical methods for identifying PZA-resistant bacteria can produce initially false results. By providing molecular techniques that have a relatively high degree of accuracy, the invention facilities the rapid detection of PZA-resistant bacteria, and augments the design of new anti-tuberculosis drugs (e.g., PZA derivatives), which requires accurate identification of the tested mycobacteria.

Derived from the discovery that *M. bovis* naturally has an altered pncA gene, the invention provides methods, primers, probes, substantially purified polypeptides, and isolated antibodies for distinguishing between *M. bovis* and *M. tuberculosis.* These methods, nucleic acids, polypeptides, and antibodies are particularly useful as epidemiological tools to monitor the spread of bovine tuberculosis to humans in geographic areas that face tuberculosis outbreaks. For commercial purposes, the primers and probes of the invention can be packaged into a kit.

The invention also provides methods for treating a mammal that is infected with PZA-resistant mycobacteria. The methods involve (i) introducing into the mycobacteria a functional pncA gene, and (ii) administering PZA to the mammal, thereby killing the mycobacteria.

BRIEF DESCRIPTION OF THE DRAWINGS

FIG. 1 is a listing of the DNA and amino acid sequences of the wild-type pncA gene of *M. tuberculosis.* The nucleotides that are altered in the altered pncA genes discussed below are indicated by bold-face type and underscoring. The complete sequence of the *M. tuberculosis* pncA gene was obtained from the 3.2 kb DNA fragment (Erdman strain) using primers designed from the sequence of the partial pncA-containing 500 bp PCR product.

FIG. 2 is a schematic representation of the pncA gene and the portions of the gene that are amplified by particular pairs of primers (P1–P8).

FIG. 3A is a restriction map of a 3.2 kb EcoRl-Pstl fragment containing the pncA. The 3.2 kb fragment was derived from cosmid DNA isolated using a 500 bp pncA-containing PCR product as a probe. The bold arrow indicates the direction of transcription for the pncA gene. Restriction endonuclease recognition sites are abbreviated as: E, EcoRi; K, KpnI; P, PstI; S, SmaI; and X, XmnI.

FIG. 3B is a pair of nucleotide sequences showing the limited homology between the genes encoding *M. tuberculosis* PZase and *E. coli* nicotinamidase.

FIG. 4 is a pair of photographs showing that the mobility of DNA corresponding to *M. bovis* differs from the mobility of DNA corresponding to *M. tuberculosis* when analyzed by PCR-SSCP. *M. bovis:* lanes 1–5, 8–15, 20–23, 24–31, 36–39, and 42. *M. tuberculosis:* lanes 6–7, 16–19, 32–35, 40–41, and 43–45.

FIG. 5 is a set of photographs showing that the mobility of DNA corresponding to PZA-resistant *M. tuberculosis* differs from the mobility of DNA corresponding to wild-type (PZA-sensitive) *M. tuberculosis* when analyzed by PCR-SSCP. To amplify the DNA electrophoresed in lanes 1–6, primers P3 (SEQ ID NO: 7) and P4 (SEQ ID NO: 8) were used. To amplify the DNA electrophoresed in lanes 7–9, primers P5 (SEQ ID NO: 9) and P6 (SEQ ID NO: 10) were used. Primers P7 (SEQ ID NO: 11) and P8 (SEQ ID NO: 12) were used to amplify the DNA that is electrophoresed in lanes 10–14. DNA amplified from PZA-resistant *M. tuberculosis* strains is electrophoresed in lanes 1–4, 5, 8, 9, and 12. As a control, DNA amplified from a wild-type (PZA-sensitive) *M. tuberculosis* strain is electrophoresed in lanes 5, 7, 10, 11, 13, and 14. The mycobacterial strains were: *M. bovis* (ATCC 19210) in lane 1; BCG Tokyo in lane 2 (provided by P. Converse, Johns Hopkins University); PZA-resistant clinical isolates of *M. tuberculosis* from Brazil in lanes 3–6 (provided by S. Morris; FDA); PZA-sensitive *M. tuberculosis* strain 12646 in lane 7; PZA-resistant *M. tuberculosis* strain derived from type strain H37Rv (ATCC 35828) in lane 8; BCG Tice in lane 9 (provided by P. Converse); PZA-sensitive *M. tuberculosis* Erdman strain in lanes 10, 11, 13, and 14 (H37728, 12646, and M40023); and PZA-resistant *M. tuberculosis* strain M3169 in lane 12.

A DETAILED DESCRIPTION OF THE INVENTION

Differentiation Between *M. bovis* and *M. tuberculosis:* In one aspect, this invention provides a method for differentiating between *M. tuberculosis* and *M. bovis* in a sample. The method involves detecting in the mycobacteria of the sample an altered pncA gene that encodes an aspartic acid residue, rather than a histidine residue, at amino acid position 57 of the PZase polypeptide encoded by the altered pncA gene. All strains of *M. bovis* that have been examined to date have this alteration, whereas this alteration has not been found in any strain of *M. tuberculosis*. Thus, an aspartic acid residue at this position is indicative of *M. bovis*, rather than *M. tuberculosis*. The aspartic acid residue at position 57 can be encoded by a change of C to G at nucleotide 169 of the altered pncA gene. Other alterations in nucleotide sequences can also result in an aspartic acid residue at position 57. For example, because of the degeneracy of the genetic code, a change of C to G at nucleotide 169 combined with a change of C to U at nucleotide 171 also will encode an aspartic acid residue at amino acid position 57.

As used herein, the term "altered" refers to any pncA nucleic acid (e.g., a gene) or PZase polypeptide that differs in nucleotide or amino acid sequence from the wild-type pncA gene of *M. tuberculosis* (or degenerate variants thereof) or the wild-type PZase polypeptide of *M. tuberculosis*. Thus, the *M. bovis* pncA gene is considered an "altered" pnca gene, even though this gene naturally confers PZA resistance. The "wild-type" *M. tuberculosis* pncA gene and the wild-type PZase polypeptide are listed in FIG. 1 (SEQ ID NO: 1 and SEQ ID NO: 2). While the nucleic acid sequences of "degenerate variants" of the pncA gene differ from the illustrated wild-type pncA sequence, the degenerate variants nonetheless encode a wild-type PZase polypeptide because most of the 20 natural amino acids are each specified by more than one codon. Thus, a "degenerate variant" of a nucleotide sequence is a nucleotide sequence that encodes the same amino acid sequence as a given nucleotide sequence, but in which at least one codon in the nucleotide sequence is different because two or more different codons can encode the same amino acid. All degenerate nucleotide sequences are included in the invention, as long as the amino acid sequence of the pncA polypeptide encoded by the nucleotide sequence is functionally unchanged. In addition, the invention includes an isolated nucleic acid encoding a polypeptide having the biological activity of an amino acid sequence of SEQ ID NO: 2 and having at least one epitope for an antibody immunoreactive with PZase polypeptide.

An isolated nucleic acid encoding an *M. tuberculosis* PZase polypeptide is included within the invention, and useful for production of the primers and probes described herein. The term "isolated" as used herein includes polynucleotides or polypeptides substantially free of other nucleic acids, proteins, lipids, carbohydrates, or other materials with which it is naturally associated. The isolated nucleic acids of the invention encoding *M. tuberculosis* PZase polypeptide include nucleic acids that encode "conservative variations" of the PZase polypeptide. A conservative variation as used herein denotes the replacement of an amino acid residue by another, biologically similar, residue. Examples of conservative variations include the substitution of one hydrophobic residue, such as isoleucine, valine, leucine, or methionine, for another, or the substitution of one polar residue for another, such as the substitution of arginine for lysine, glutamic acid for aspartic acid, or glutamine for asparagine, and the like. The term "conservative variation" also includes the use of a substituted amino acid in place of an unsubstituted parent amino acid, provided that antibodies raised to the substituted polypeptide also immunoreact with the unsubstituted polypeptide. Also include are isolated nucleic acids that encode a portion or fragment of the PZase polypeptide, as long as the PZase polypeptide retains a biological activity of the full length PZase polypeptide, such as the ability to convert PZA to pyrazinoic acid (Konno et al., Am. Rev. Respir. Dis. 95, 461–469 (1967)). Such nucleic acids include naturally-occurring, synthetic, and intentionally manipulated polynucleotides. For example, portions of the mRNA sequence may be altered due to alternate promoters for RNA transcription. As another example, pncA nucleic acids may be subjected to site-directed mutagenesis. Antisense sequences for pncA also are included.

Any of the various art-known methods for detecting point mutations can be used to detect the altered *M. bovis pncA* gene. Now that the alteration in the *M. bovis* sequence has been identified and appreciated, a person of ordinary skill in molecular biology can readily identify *M. bovis* using any conventional method for detecting point mutations. The term "detecting" as used herein encompasses any means for determining the presence of a given gene or polypeptide in a sample. For example, an altered pncA gene can be detected by methods such as, but not limited to, polymerase chain reaction single-strand conformation polymorphism (PCR-SSCP (Orita et al., 1989, Genomics 5: 874–879)), single-strand conformation polymorphism (SSCP (Orita et al., 1989, Proc. Natl. Acad. Sci. 86: 2766–2770)), DNA sequencing, DNA hybridization (e.g., Southern blotting, dot/slot blotting, colony hybridization), denaturing gradient gel electrophoresis (Myers et al., 1985, Nature, 313: 495–498), ligase-mediated gene detection (Landegren et al., 1988, Science 241: 1077–1080), and RNase digestion of an RNA/DNA duplex (Winter et al., 1985, Proc. Natl. Acad. Sci. 82: 7575–7579).

Now that applicants have shown that PZA resistance in *M. bovis* is conferred by an alteration the pncA gene and PZase, it is recognized for the first time that immunoassays can be used to distinguish *M. bovis* from *M. tuberculosis*. Therefore, the invention includes an isolated polyclonal or monoclonal antibody that preferentially binds the *M. bovis* PZase polypeptide. "Isolated antibodies" are those antibodies that are separated from the animal in which they were raised (e.g., a rabbit or mouse) or antibodies that were produced in vitro. Suitable immunoassays include Western blot analysis, slot or dot blot assays, ELISAs, immunoprecipitation assays, and the like. "Antibody" means an immunoglobulin protein that is capable of binding an antigen. The term antibody is meant to include antibody fragments (e.g., F(Ab')$_2$, FAb', FAb) capable of binding the epitope or antigen of interest. The term "preferentially binds" means high avidity and/or high affinity binding of an antibody to a specific antigen or epitope. Antibody binding to an epitope on this specific antigen is stronger than binding of the same antibody to any other antigen or epitope. In particular, an antibody that preferentially binds M. bovis PZase binds M. bovis PZase more strongly than it binds M. tuberculosis PZase. In addition, an antibody that preferentially binds an antigen or epitope binds that antigen or epitope more strongly than it binds other molecules that may be present in the same sample as the antigen of interest. Antibodies that bind preferentially to a polypeptide of interest may be capable of binding other polypeptides at a weak, yet detectable, level (e.g., 10% or less of the binding shown to the antigen of interest). Such weak binding, or background binding, is readily discernible from the specific antibody binding to the polypeptide of interest, e.g., by use of appropriate controls.

Also included in the invention is a substantially pure M. bovis PZase polypeptide, or a conservative variant thereof. Such a polypeptide can be used to produce the above-described antibodies that are useful in immunoassays. The term "substantially pure polypeptide" means a preparation of a PZase polypeptide that is substantially free from the proteins and other naturally occurring organic molecules with which PZase is naturally associated. This typically means that the desired PZase polypeptide constitutes at least 60% of the dry weight of the preparation. Preferably, the preparation is at least 75%, more preferably at least 90%, and most preferably at least 99%, by weight, PZase polypeptide. A substantially pure PZase polypeptide may be obtained, for example, by extraction from a natural source (e.g., M. bovis); by expression of a recombinant nucleic acid encoding a PZase polypeptide; or by chemical synthesis. Purity can be measured and/or obtained by any appropriate method, e.g., column chromatography, polyacrylamide gel electrophoresis, or HPLC.

A protein is substantially free of naturally associated components when it is separated from those contaminants that accompany it in its natural state. Thus, a protein that is chemically synthesized, or produced from a source different from the source from which the protein naturally originates, will be substantially free from its naturally associated components. Accordingly, substantially pure PZase includes recombinant PZase synthesized, for example, in vitro in a mammalian cell line, in E. coli or another single-celled microorganism, or in insect cells.

PCR-Single-Strand Conformation Polymorphism (PCR-SSCP): The preferred method for detecting an alteration in the pncA gene is "PCR-SSCP." In this method, a portion of the pncA gene is PCR amplified using primers that flank the alteration in the gene. The amplified DNA then is analyzed by gel electrophoresis under non-denaturing conditions. An alteration in the amplified DNA can be detected as an alteration in the mobility of the altered DNA through the gel, relative to the mobility of wild-type DNA. The term "amplifying" means to reproduce a nucleic acid, e.g., by DNA synthesis. For example, an amplified DNA molecule is one that reproduced such that the total number of copies of the particular DNA molecule is increased. Typically, amplification is accomplished by incubating a nucleic acid polymerase (e.g., DNA polymerase or Taq polymerase) with non-polymerized nucleotides (e.g., DATP, dCTP, dGTP, and dTTP), and a suitable buffer with a single-stranded nucleic acid template of the DNA to be amplified. For convenience, such amplification can be accomplished by "polymerase chain reaction" (PCR), in which a nucleic acid is synthesized in the presence of a thermostable polymerase (e.g., Taq polymerase), a large number of suitable nucleic acid primers and non-polymerized nucleotides (see Sambrook et al., supra). In a typical PCR reaction, (1) the strands of a double-stranded DNA molecule are separated by heating the DNA to produce single-stranded nucleic acid templates, (2) the temperature of the reaction is lowered, and the nucleic acid primers are annealed to single-strand nucleic acid templates, (3) DNA synthesis ensues, such that a double-stranded molecule is produced from each original single-stranded template, and steps (1–3) are repeated for numerous cycles (typically 35 cycles). Now that altered pncA genes have been identified and appreciated as indicators of PZA resistance, those of ordinary skill in the art of molecular biology can readily use DNA amplification techniques to amplify the pncA gene without undue experimentation.

Typically, the primers for PCR-SSCP are designed such that they can amplify a portion of the gene that is approximately 200 bp in length (e.g., a 100–500 bp, preferably, a 150–200 bp portion). Preferably, the altered nucleotide is approximately centered within the amplified sequence. The exact portion of the pncA gene that is amplified is not critical to the success of this method, provided that the amplified portion encompasses the alteration in the genomic nucleic acid that confers PZA resistance (e.g., in the case of M. bovis, the amplified portion should include the coding sequence of amino acid 57 of the PZase polypeptide). An example of a pair of primers that can be used to amplify a suitable portion of the pncA gene for identifying M. bovis is:

5'-GATTGCCGACGTGTCCAGAC-3' (SEQ ID NO: 3) and

5'-ATCAGCGACTACCTGGCCGA-3' (SEQ ID NO: 4). Sequences that are "substantially complementary" to these sequences also are useful for amplifying an appropriate portion of a nucleic acid of the mycobacterium that is being identified. This means that the primers must be sufficiently complementary to hybridize with their respective strands under conditions that allow the agent for polymerization to perform. In other words, the primers should have sufficient complimentarity with the 5' and 3' sequences flanking a portion of the mycobacterial nucleic acid that encompasses an the alteration that confers PZA resistance. The mycobacterial sequences to which the primers hybridize are considered the "target" flanking 5' and 3' polynucleotide sequences, as they flank the sequence that is to be amplified. Primers having "substantially the sequence" of the target polynucleotides differ in sequence from the target polynucleotide sequence, yet permit hybridization of the primer.

PCR amplification of the altered pncA gene can be carried out in accordance with conventional PCR-SSCP protocols (see Orita et al., supra). For convenience, a labeled nucleotide (e.g., Sambrook, et al., Cold Spring Harbor Laboratory Press, 2nd Edition, (1989)) can be incorporated into the DNA that is amplified by PCR. Incorporation of a labeled nucleotide facilitates detection of the amplified DNA directly in a gel, and obviates the need for transferring the DNA from a gel onto a membrane. Once the DNA is amplified, it is denatured. Typically, denaturation will be accomplished by heating the DNA to 80°–100° C. for 5–10 minutes in the presence of formamide dye (95% formamide, 20 mM EDTA, 0.05% bromphenol blue, and 0.05% xylene cyanol). The heated, amplified DNA then is immediately cooled by incubating the DNA on ice for 5–10 minutes in order to prevent the DNA from renaturing.

In PCR-SSCP, the denatured, amplified DNA is electrophoresed on a gel under non-denaturing conditions. For amplified DNA fragments of approximately 200 bp, an example of a suitable gel is a 20% polyacrylamide/5% glycerol gel (16×20 cm) pre-chilled to 4° C. and electrophoresed at 4° C. at 5 W in 0.5 X TBE buffer. The electrophoresed DNA then can be detected by conventional methods (e.g., ethidium bromide staining, DNA hybridization, or in-gel detection of labeled DNA). Typically, the gel will include, as a control, DNA that is amplified from a known stock of M. tuberculosis and/or M. bovis. A detailed working example of this method is provided below.

The invention is suitable for distinguishing between M. bovis and M. tuberculosis in any of a variety of samples containing or believed to contain mycobacteria.

For example, the mycobacteria can be contained within a biological fluid or tissue (e.g., sputum, blood, lung tissue) of a mammal (e.g., a human or cow). Alternatively, an in vitro culture of mycobacteria, (e.g., a tissue culture of mammalian cells that are infected with mycobacteria) can serve as the sample. Because PCR can be used to amplify a portion of the altered pncA gene, the sample can, in principle, contain a single mycobacterium. If desired, mycobacteria obtained from a mammal can be cultured in vitro according to conventional methods prior to assaying the mycobacteria for an altered pncA gene. Likewise, the pncA gene from a mycobacteria sample of interest can be cloned into a genetic vector prior to assaying for an alteration in the gene, if desired. In addition, any of the conventional methods for identifying M. bovis can be used in conjunction with this method for distinguishing M. bovis from M. tuberculosis.

Use of Hybridization Methods to Identify M. bovis: As an alternative to using PCR-SSCP to distinguish M. bovis from M. tuberculosis, traditional nucleic acid hybridization methods can be used to identify M. bovis. Thus, a nucleic acid probe(s) for use in a nucleic acid hybridization method(s) is included within the invention. Such a "probe" is a nucleic acid molecule (DNA or RNA) that includes a nucleotide sequence that is complementary to a portion of (i.e., capable of forming Watson-Crick base-pairs with part of) a wild-type or altered pncA gene, where the portion includes a nucleotide sequence encoding an aspartic acid residue at amino acid position 57 of the PZase polypeptide. A nucleic acid portion that is substantially complementary to the aforementioned probe is also useful as a probe, and thus is included within the invention. In a preferred embodiment, the invention includes a probe that is complementary to a portion of the M. bovis pncA gene that includes a G, rather than a C, at nucleotide 169. In another preferred embodiment, the probe is complementary to a portion of the M. tuberculosis pncA gene that includes a C at nucleotide 169. In other words, a probe that is complementary to either the wild-type or altered pncA genes is useful, and those skilled in the art will appreciate the results obtained with either type of probe.

Under typically stringent hybridization conditions, a probe that is complementary to the wild-type pncA gene will hybridize to (i.e., Watson-Crick base-pair with) the pncA gene of M. tuberculosis, but not the pncA gene of M. bovis. Thus, the inability of such a probe to hybridize to DNA in a sample indicates that the sample includes M. bovis. Inversely, a probe that includes a sequence that is complementary to the alteration in the M. bovis pncA gene will hybridize preferentially to the altered M. bovis gene rather than the wild-type M. tuberculosis gene. Those skilled in the art will know how to design appropriate controls for such assays (e.g., include a nucleic acid sample from a known mycobacterium and include a probe that hybridizes to a region of the pncA that is common to M. tuberculosis and M. bovis). A typical probe consists of a chain of 8 to 20 ribonucleotides or deoxyribonucleotides, and is complementary to a portion of the pncA gene that is a chain of 8 to 20 deoxyribonucleotides. The position of the alteration along the length of the probe is not critical. If desired, the probes can be detectably labelled. Those of ordinary skill in the art will know or can readily ascertain various techniques for labelling nucleic acid probes.

Identification of PZA-resistant Mycobacteria: The invention also provides methods for identifying PZA-resistant mycobacteria generally. As discussed above, PZA-resistant strains of mycobacteria complicate efforts to treat and contain the spread of tuberculosis. Now that the molecular basis for PZA resistance has been revealed by the experiments described below, molecular-based assays can be used to identify PZA-resistant mycobacteria. Included are those mycobacteria that are naturally resistant to PZA, as well as those mycobacteria that acquire PZA resistance.

In principle, this aspect of the invention is a variation of the above methods for distinguishing between M. bovis and M. tuberculosis. For the first time, the scientific basis for PZA-resistant strains of mycobacteria has been discovered by applicants who have shown that these strains fail to encode a functional PZase polypeptide due to an alteration (s) in the pncA gene. Thus, as above for M. bovis, this aspect of the invention involves detecting an "altered" pncA gene in a mycobacterium as an indicator of PZA resistance.

As is described in detail in the examples below, several pncA gene alterations that confer PZA resistance have now been identified. These alterations are summarized in Table 1.

TABLE 1

Mutations in the *pncA* Gene of PZA-reistant *M. tuberculosis*

| Strain | pncA Mutation | PZA susceptibility[a] | MIC For PZA[b] | MDR[c] |
|---|---|---|---|---|
| PZA-R | Deletion of G 288[d] | – | >500 μg/ml | – |
| Vertullo | Deletion of G 162 | – | >500 μg/ml | + |
| F36946 | Asp 63 → His | – | >500 μg/ml | + |
| M3S169 | Gln 141 → Pro | – | >500 μg/ml | + |
| M36470 | Cys 138 → Ser | – | >500 μg/ml | + |

[a]Determined according to the method of McDermott and Tomsett, 1954, Am. Rev. Tuberc. 70:748–754
[b]MIC: Minimal Inhibitory Concentration
[c]MDR: Multi-Drug Resistance against INH and rifampicin
[d]The amino acid positions referred to herein are numbered with respect to the full-length wild-type M. tuberculosis PZase polypeptide. The position of these amino acids may be different in altered PZase polypeptides.

In each of strains PZA-R and Vertullo, the deletion of a nucleotide results in a "−1 frameshift" in the translational reading frame of the mRNA encoded to the genes. In other words, because of the −1 frameshift at position 288, the pncA gene of the PZA-R strain encodes proline-valine-threonine (and so forth), rather than proline-glycine-aspartic acid at residues 54–56. Similarly, because of the −1 frameshift at position 162, the pncA gene of the Vertullo strain encodes lysine-cysteine-leucine (and so forth), rather than lysine-glycine-alanine at residues 96–98.

Now that alterations in the pncA gene of PZA resistant mycobacteria have been identified and shown to be responsible for PZA resistance, PZA-resistant strains of mycobacteria can readily be identified by employing methods analogous to those described above for identifying *M. bovis*. In addition, new PZA-resistant strains having as yet unidentified specific alterations the pncA gene can be readily identified by those of ordinary skill without resort to undue experimentation. For example, where a mycobacterium is found to be PZA resistant, but does not contain one of the particular alterations in the PZA gene described herein, it is reasonable that such mycobacterium contains a new alteration in its PZA gene. This alteration can be readily and specifically identified, for example, by nucleic sequencing and comparing the sequence determined to the wild-type pncA nucleotide sequence.

As is the case for identifying *M. bovis*, PCR-SSCP is a preferred method for identifying PZA-resistant mycobacteria because this method is rapid and reproducible. Included within the invention is a series of overlapping primers that is particularly useful for detecting alterations in the pncA gene by PCR-SSCP. These primers permit amplification of the entire pncA gene; thus, they are useful for identifying any alteration in the pncA gene. These primers include

P1: 5'-GCTGGTCATGTTCGCGATCG-3' (SEQ ID NO: 5);

P2: 5'-TCGGCCAGGTAGTCGCTGAT-3' (SEQ ID NO: 6);

P3: 5'-CGTCGACGTGCAGAACGACT-3' (SEQ ID NO: 7);

P4: 5'-GATTGCCGACGTGTCCAGAC-3' (SEQ ID NO: 8);

P5: 5'-ACCGGACTATTCCTCGTCGT-3' (SEQ ID NO: 9);

P6: 5'-GCGCACACAATGATCGGTGG-3' (SEQ ID NO: 10);

P7: 5'-GCGGCTTCGAAGGAGTCGAC-3' (SEQ ID NO: 1); and

Figure 2:
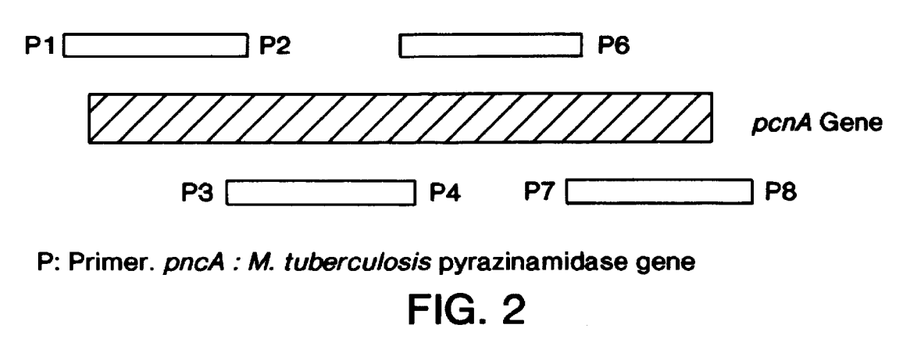

P8: 5'-GCTTTGCGGCGAGCGCTCCA-3' (SEQ ID NO: 12); and sequences substantially complementary thereto. The relationship between these primers and the pncA gene is shown schematically in FIG. 2; the portion of the pncA gene that is amplified by particular pairs of primers is indicated.

Now that alterations in the pncA gene have been identified and recognized as conferring PZA resistance to mycobacteria, nucleic acid hybridization methods can also be used to identify PZA-resistant mycobacteria. Accordingly, the invention includes a nucleic acid probe(s) (DNA or RNA) for identifying a PZA-resistant mycobacterium. The probe (typically 8–20 nucleotides) includes a nucleic acid that is complementary to a portion (typically 8–20 nucleotides) of an altered pncA gene of a PZA-resistant mycobacterium, where the portion confers PZA-resistance. Included are nucleic acid probes that are complementary to a portion of the pncA gene that (i) results in a –1 frameshift at amino acid position 96; (ii) results in a –1 frameshift at amino acid position 126; (iii) encodes a histidine residue at amino acid position 63; (iv) encodes a serine residue at amino acid position 138; and (v) encodes a proline residue at amino acid position 141. Specific examples include those probes that are complementary to a portion of an altered pncA gene that comprises (i) a deletion of nucleotide 288; (ii) a deletion of nucleotide 162; (iii) a change of G to C at nucleotide 187; (iv) a change of T to A at nucleotide 412; and (v) a change of A to C at nucleotide 422. These probes, when used in hybridization methods, will hybridize preferentially to altered pncA genes. Thus, these probes can be used to distinguish PZA-resistant mycobacteria from PZA-sensitive mycobacteria by hybridizing the probes to nucleic acids (i.e., DNA or RNA) of the mycobacteria under stringent hybridization conditions. Probes that are complementary to the wild-type pncA sequences can also be used to detect PZA-resistant mutants when the probes are designed to include a sequence that confers PZA resistance when the sequence is altered.

The deletion of a single nucleotide in each of the PZA-R and Vertullo strains of *M. tuberculosis*, described above, results in –1 frameshift during synthesis of the altered PZase polypeptide encoded by the altered pncA gene. Based upon the nucleotide sequence of the pncA gene of the PZA-R strain, the –1 frameshift results in a PZase polypeptide that is 126 amino acids in length, rather than a full-length 186 amino acids. Similarly, the –1 frameshift of Vertullo results in a truncated PZase polypeptide of 117 amino acids. These PZA-resistant strains of mycobacteria and their homologs can also be detected in immunoassays that employ antibodies, especially monoclonal antibodies, that specifically bind the carboxy-terminal portion of wild-type PZase that is missing in the truncated PZase polypeptides. Thus, the altered PZase polypeptides of PZA-resistant mycobacteria having the alterations fail to be bound by such antibodies, even though the altered PZase polypeptides would be bound by antibodies that specifically bind epitopes at the amino-terminal portion of the polypeptides.

In principle, immunoassays can also be easily developed and used to identify PZA-resistant strains of mycobacteria, because a single amino acid alteration also can produce an epitope(s) that is specific to the altered PZase polypeptide. Also, a truncated, or even elongated, PZase polypeptide that arises from a frameshift can have an amino acid sequence that, at least in part, differs significantly from that of wild-type *M. tuberculosis* PZase polypeptide. Such is the case for the PZase polypeptides of the Vertullo and PZA-R strains of *M. tuberculosis* because of the –1 frameshifts resulting from the deletion of nucleotides 162 and 288, respectively. Thus, these PZase polypeptides can be distinguished from wild-type PZA in immunoassays that employ antibodies that preferentially bind the portion of the polypeptide that is altered as a result of the translational frameshift.

Accordingly, the invention includes isolated antibodies useful in performing immunoassays for identifying a PZA-resistant mycobacterium. In particular, the invention includes an isolated polyclonal or monoclonal antibody that preferentially binds an altered PZase polypeptide that confers PZA resistance, such as a PZase polypeptide of an *M. tuberculosis* strain homologous to an *M. tuberculosis* strain selected from the group consisting of M36470, M3S169, F36946, Vertullo, and PZA-R. The term "homologous" is meant to include strains of mycobacteria that have PZase polypeptides that are identical to, or conservative variations of, the PZase polypeptides of the recited strains. Such homologous strains of mycobacteria can differ from the recited strains at any genetic locus, provided that the homologous strain is capable of causing respiratory tuberculosis in mammals, and is rendered PZA-resistant by an altered pncA gene. Included by the term "homologous" are the recited strains themselves, namely, M36470, M3S169, F36946, Vertullo, and PZA-R.

The invention also includes a substantially pure altered PZase polypeptide that confers PZA resistance, or a conservative variant thereof. Specific examples of such polypeptides are the PZase polypeptides of the M36470, M3S169, F36946, Vertullo, and PZA-R strains of *M. tuberculosis* and strains homologous thereto. In other words, any PZase polypeptides having the alterations summarized in Table 1 are expected to confer PZA resistance, and are included within the invention.

In another aspect, the invention provides a method for treating a mammal that is infected with PZA-resistant mycobacteria (e.g., *M. bovis* or PZA-resistant *M. tuberculosis*); thus, this aspect of the invention provides a method for treating tuberculosis. The method involves introducing a pncA gene that encodes a functional PZase polypeptide into at least a portion (preferably at least 10%, more preferably at least 50%, and most preferably at least 75%) of the PZA-resistant mycobacteria that infect the mammal. A PZase polypeptide is considered "functional" if it retains a biological activity of the full length PZase polypeptide, namely the ability to convert PZA to pyrazinoic acid. Expression of the pncA gene in the PZA-resistant mycobacteria renders the mycobacteria sensitive to PZA. The mammal then is administered a therapeutically effective amount of PZA, which inhibits or kills at least a portion of the mycobacteria that infect the mammal. A treatment that "inhibits" the mycobacteria slows or prevents the growth or reproduction of the bacteria inside the infected mammal and/or decreases or prevents the production of release of mycobacterial toxins into the cells of the infected mammal. Generally, the terms "treating," "treatment," and the like are used herein to mean obtaining a desired pharmacologic and/or physiologic effect. The effect may be prophylactic in terms of completely or partially preventing a mycobacterial infection or disease (e.g., tuberculosis) or sign or symptom thereof, and/or may be therapeutic in terms of a partial or complete cure for an infection or disease and/or adverse effect attributable to the infection or disease. "Treating" as used herein covers any treatment of an infection or disease in a mammal, particularly a human, and includes:

(a) preventing the disease from occurring in a subject that may be predisposed to the disease, but has not yet been diagnosed as having it;

(b) inhibiting the infection or disease, i.e., arresting its development; or (c) relieving or ameliorating the infection or disease, i.e., cause regression of the infection or disease. The invention is thus directed to treating patients who are afflicted with a mycobacterial infection or tuberculosis. More specifically, "treatment" is intended to mean providing a therapeutically detectable and beneficial effect on a patient suffering from a mycobacterial infection or tuberculosis.

The term "introducing" a pncA gene into a mycobacterium means to insert a pncA gene into the mycobacterium such that the pncA gene is available to be expressed by the cellular machinery (e.g., polymerases and ribosomes) of the mycobacterium. The pncA gene can be introduced into mycobacteria by using standard recombinant DNA techniques to insert the pncA gene into a mycobacteriophage, such as mycobacteriophage L5, L1, or D29 (Hatfull and Jacobs, Mycobacteriophages: Cornerstones of Mycobacterial Research. In Tuberculosis. (ed) B. R. Bloom, ASM Press, Washington, D.C.). A therapeutically effective amount of the pncA gene then is administered to the infected mammal, and a therapeutically effective amount of PZA is administered to the mammal. The term "therapeutically effective" means sufficient pncA gene to produce PZase to thereby render the mycobacteria resistant to PZA. It is believed that one copy of the pncA gene per organism would render the organism sensitive to PZA. Various means can be used to "administer" PZA or a pncA gene to a mammal as a therapeutic. Generally, the therapeutic to be delivered can be formulated into a pharmaceutical composition by admixture with a pharmaceutically acceptable non-toxic excipient or carrier (e.g., saline). In practicing the invention, the therapeutic can be prepared for use in parenteral administration (e.g., for intravenous injection or intra-arterial injection). Preferably, the pncA gene is administered to the mammal intranasally or intrabronchially, e.g., as a liquid or aerosol formulation (e.g., nasal drops or spray) in a pharmaceutically acceptable excipient. Preferably, PZA is administered orally or according to other conventional methods. While the optimal therapy regime can be determined for each treated mammal (e.g., a human or cow), a typical regime involves administration of $10^6$ to $10^8$ pfc of mycobacteriophage carrying the pncA gene, 1 to 7 times weekly for a period of 3 to 12 (preferably 6–12) months, or until the signs and symptoms of the mycobacterial infection or tuberculosis are ameliorated. PZA typically is administered daily (in combination with isoniazid and rifampicin, if desired) for the first two months although alternative PZA treatment regimes can be used (Mitchison et al., 1985, Tubercle 66: 219–225). If desired, this therapy regime can be used in conjunction with conventional methods, such as administration of at least one other mycobacterial therapeutic agent (e.g., isoniazid and/or rifampicin).

Included within the invention is a kit(s) for distinguishing *M. bovis* from *M. tuberculosis* or for identifying PZA-resistant mycobacteria. Such a kit is a package that carries a container(s) that contains any or all of the primers and probes described above. Preferably, the kit also contains isolated nucleic acid(s) corresponding to all or a portion of the wild-type *M. tuberculosis* pncA gene and/or an altered pncA gene (e.g., from *M. bovis* or one of the acquired PZA-resistant *M. tuberculosis* strains, such as Vertullo). A kit can contain the above-described monoclonal or polyclonal antibodies useful for identifying PZA-resistant mycobacteria. Typically, the nucleic acids, antibodies, and polypeptides that are contained within the kits are present in a measured amount that is indicated on a label(s) on the container within the kit. In addition, a typical kit includes a set of instructions for practicing the methods of the invention. Nucleic acids, antibodies, and polypeptides that are useful as controls can also be included in a kit of the invention.

SUMMARY OF THE EXAMPLES

Several working examples are provided below. These examples describe (i) the cloning of the *M. tuberculosis pncA* gene, (ii) identification of the alterations in the pncA gene that confer PZA resistance, (iii) use of the pncA gene to render PZA-resistant *M. tuberculosis* sensitive to PZA, (iv) use of PCR-SSCP to rapidly differentiate between *M. bovis* and *M. tuberculosis,* and (v) use of PCR-SSCP to identify PZA-resistant *M. tuberculosis* strains. Before describing the examples in further detail, a description of the materials and methods used in these examples is provided.

Materials and Methods

Mycobacterial strains and DNA. Strains of *M. tuberculosis, M. bovis,* and BCG were grown in 7H9 liquid medium with ADC (Albumin-Dextrose-Catalase) enrichment at 37° C. for 2–4 weeks. The PZA-resistant *M. tuberculosis* strain (ATCC 35828) derived from type strain H37Rv was obtained from American Type Culture Collection. PZA-resistant clinical isolates were provided by L. Heifets (National Jewish Center for Immunology and Respiratory Diseases, Denver, Colo.), J. Belisle and P. Brennan (Colorado State University). Genomic DNA from *M. tuberculosis* strains and other mycobacterial species was isolated as described previously (Zhang, et al., Infect. Immun. 60, 2160–2165 (1992)). Genomic DNA from *M. bovis* strains was provided by V. P. Shankar (Texas A & M University Health Science Center).

Cloning and characterization of the *M. tuberculosis pncA* gene. To clone the *M. tuberculosis pncA* gene, degenerate primers were designed based on the putative *E. coli* nicotinamidase amino acid sequence (Jerlstrom, et al., Gene 78, 37–46 (1989)). When cloned into a plasmid vector, the putative *E. coli pncA* indeed expresses functional nicotinamidase activity upon transformation into a *Salmonella typhimurium pncA* mutant strain JF49 (Foster et al., J. Bacteriol., 137, 1165–1175 (1979)). The forward primer was designed from the 9–17 amino-acid residues VDLQNDFCA (SEQ ID NO: 13), and the reverse primer from the 168–179 amino-acid residues GYKVNVITDGC (SEQ ID NO: 14), of the *E. coli* enzyme (Jerlstrom, et al., Gene 78, 37–46 (1989)). PCR was performed using the above primers with genomic DNA from a PZA-susceptible *M. tuberculosis* strain as template (Saiki, et al., Science 239, 487–491 (1988)). A 500 bp PCR product was obtained, and sequence analysis showed that it contained a partial open reading frame with homology to the *E. coli* nicotinamidase gene described above. A cosmid clone containing the complete *M. tuberculosis pncA* gene was isolated using the $^{32}$P-labelled 500 bp PCR product containing the partial pncA gene as a probe, by screening an integrating mycobacterial shuttle cosmid DNA library constructed from the *M. tuberculosis* Erdman strain (provided by W. R. Jacobs, Albert Einstein College of Medicine, New York). Restriction mapping of the cosmid DNA, followed by Southern blot analysis using the 500 bp PCR product as a probe, and transformation studies localized the *M. tuberculosis pncA* gene on a 3.2 kb EcoRI-PstI fragment, which subsequently was subcloned into pUC19. The standard molecular biology techniques were carried out as described previously (Sambrook, et al., Cold Spring Harbor Laboratory Press, Cold Spring Harbor, N.Y., 1989).

The complete *M. tuberculosis pncA* sequence (from *M. tuberculosis* Erdman strain) (accession number under application) was determined from the 3.2 kb EcoRI-PstI fragment using primers derived from sequences of the 500 bp pncA-containing PCR product. The determination of pncA sequences from *M. bovis,* BCG and other *M. tuberculosis* strains was performed by PCR direct sequencing using primers designed from the above-described complete *M. tuberculosis pncA* sequence in an automatic DNA sequencer. The sequence homology alignment between *M. tuberculosis* and *E. coli* PncA sequences was performed using a FASTA algorithm.

Transformation of tubercle bacilli. The pncA plasmid construct for transformation of PZA-resistant BCG and H37Rv was made as follows. The 3.2 kb EcoRI-PstI fragment containing the functional *M. tuberculosis pncA* was cloned into the hygromycin mycobacterial shuttle vector p16R1 (Garbe, et al., Microbiology 140, 133–138 (1994)) as described (Sambrook, et al., Cold Spring Harbor Laboratory Press, Cold Spring Harbor, N.Y., 1989). Both the p16R1 3.2 kb pncA construct and the cosmid DNA containing the functional *M. tuberculosis pncA* gene, along with the vector controls, were transformed by electroporation into the naturally PZA-resistant *M. bovis* BCG and PZA-resistant *M. tuberculosis* H37Rv as described (Zhang, et al., Mol. Microbiol. 88, 521–524 (1993)).

PZase enzyme assay. Pyrazinamidase activity was assayed according to the method of Wayne (Wayne, Am. Rev. Respir. Dis. 109, 147–151 (1974)). Briefly, a heavy bacterial inoculum (several loopfuls) was inoculated onto the surface of Dubos agar (Difco) containing 0.1 mg/ml PZA in a test tube, which was then incubated at 37° C. for 4 days. Two milliliters of 1 % ferrous ammonium sulfate were added, and the test tubes were incubated at 4° C. for 1–2 hours. A positive PZase activity appeared as a brownish band in the agar surface. A positive culture (PZA-sensitive *M. tuberculosis* strain H37Rv) and a negative culture (BCG Pasteur) were included as controls.

PZA susceptibility testing. The susceptibility to PZA of recombinant mycobacterial strains was tested in 7H9 liquid medium adjusted to acid pH (5.6) as described elsewhere (McDermott, et al., Am. Rev. Tuberc. 70, 748–754 (1954)). Briefly, 2 week old liquid mycobacterial cultures (about $10^{7-8}$ bacilli) were diluted at $10^{-3}$ and $10^{-5}$ in acid 7H9 liquid medium (pH 5.6) containing 50, 100, 200, 500, 1000 μg/ml PZA in Eppendorf tubes. Each strain tested for PZA susceptibility was in duplicate. The Eppendorf tubes were then incubated at 37° C. for 2–3 weeks when the extent of growth inhibition was assessed. PZA susceptible H37Ra or H37Rv, and PZA-resistant BCG were included as sensitive and resistant controls, respectively.

Macrophage infections with mycobacteria and assay of PZA susceptibility of intracellular mycobacteria were performed as described (Skinner, et al., Antimicrob Agent Chemother, 38, 2557–2563 (1994)). Briefly, $5 \times 10^5$ J774 murine macrophages were infected with $2-5 \times 10^6$ bacteria in 24-well tissue culture plates. Each mycobacterial strain used for macrophage infection was in triplicate. After infection at 37° C. for 1–2 hours, the extracellular bacteria were washed off with PBS twice. Tissue culture medium (RPMI 1640) containing various concentrations of PZA or streptomycin was added to the infected macrophages and the plates were incubated in a $CO_2$ incubator at 37° C. for 1–2 weeks. The number of intracellular bacteria was counted under the microscope and expressed as an average of at least 50 infected macrophages per well for all three triplicate wells for each bacterial strain.

EXAMPLES

Figure 3A:
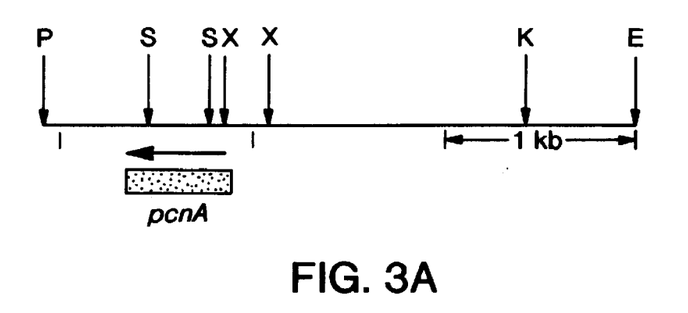
Figure 3B:
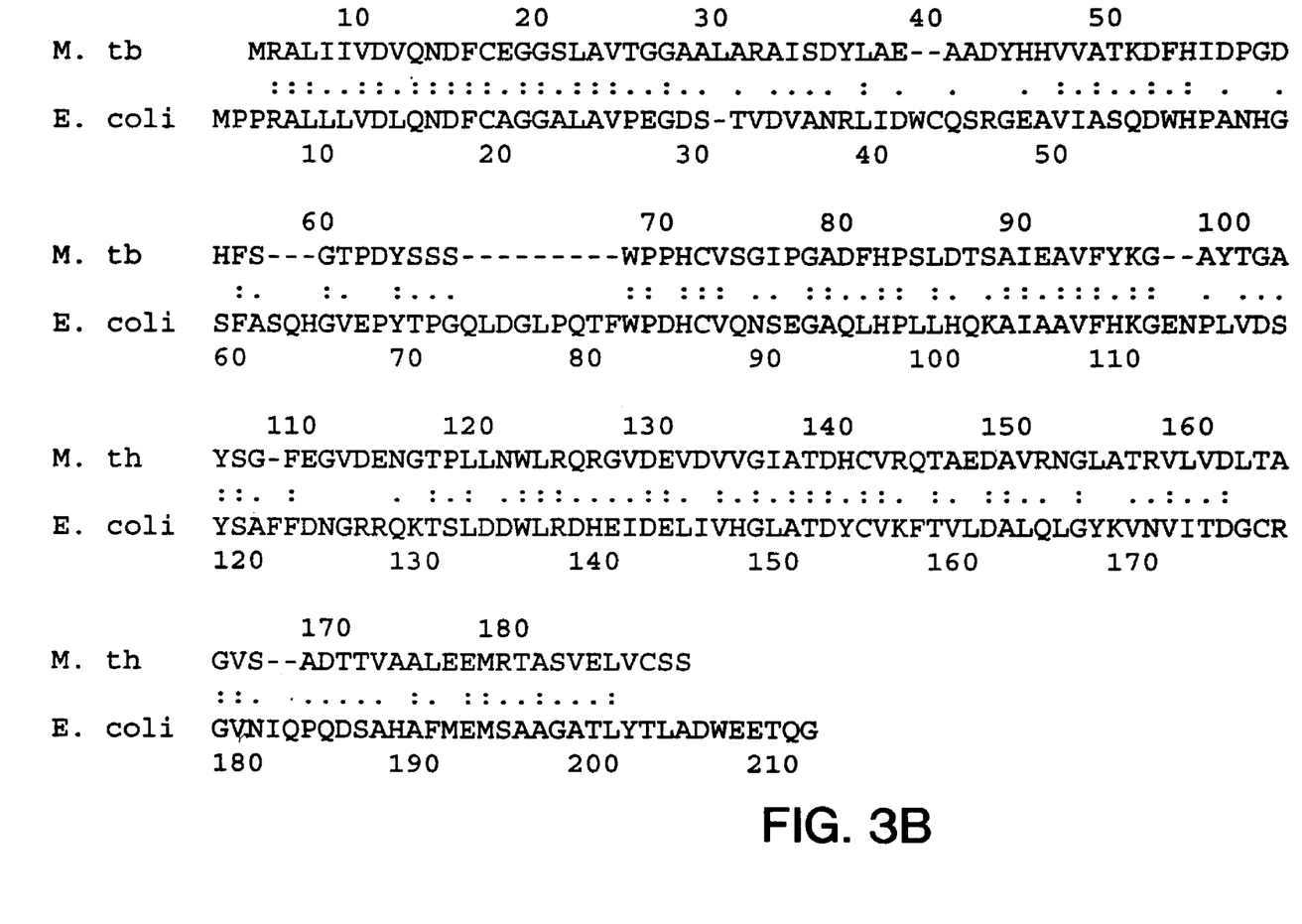
Figure 4:
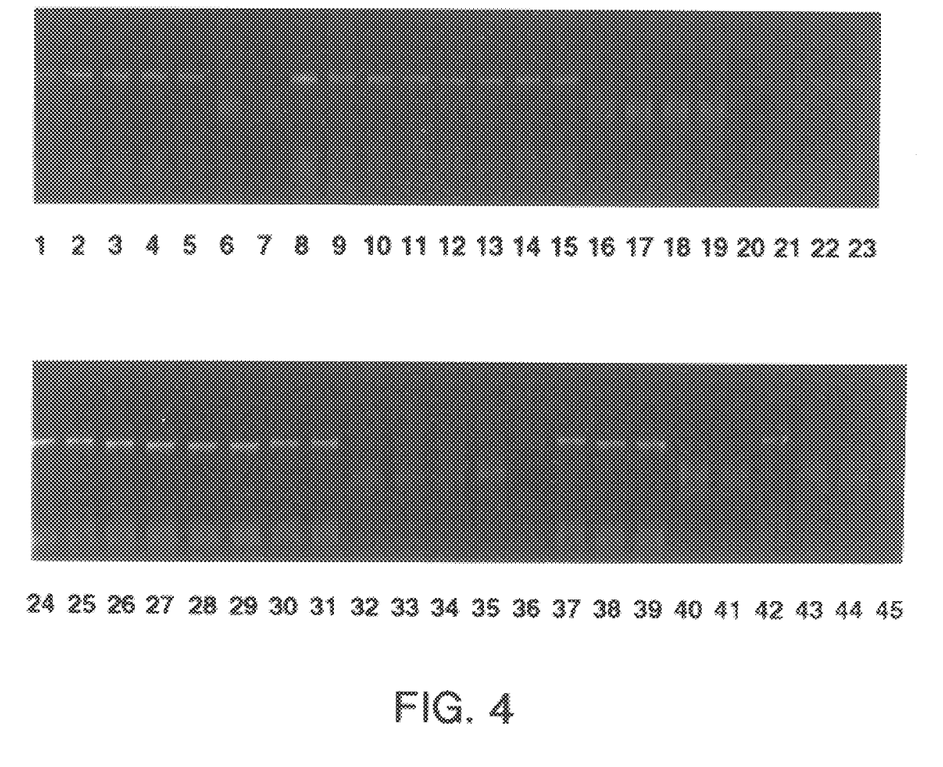
Figure 5:
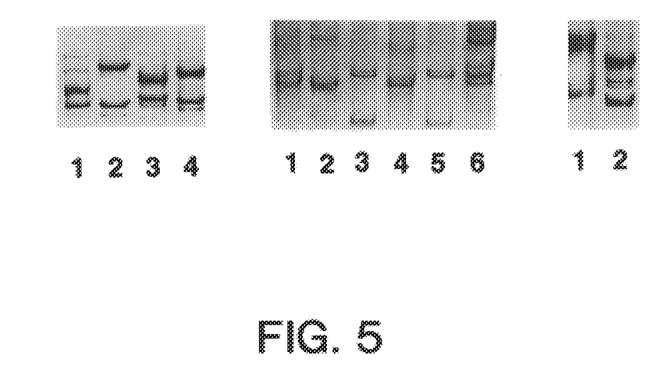

Cloning and characterization of the *M. tuberculosis pncA* gene. The *M. tuberculosis pncA* gene was cloned by PCR using degenerate primers based on the amino acid sequence derived from the *E. coli* nicotinamidase gene (pncA) (Jerlstrom, et al., Gene 78, 37–46 (1989)). The *M. tuberculosis pncA* was initially cloned on a 500 bp PCR product from a PZA-susceptible *M. tuberculosis* strain. Sequence analysis showed that the PCR product contained a partial open reading frame with homology to the *E. coli* nicotinamidase sequence (Jerlstrom, et al., Gene 78, 37–46 (1989)). To obtain the complete *M. tuberculosis pncA* gene, an *M. tuberculosis* integrating cosmid DNA library was screened using the 500 bp pncA-containing PCR product as a probe. A pncA-hybridizing cosmid clone was isolated and used to transform BCG, an attenuated vaccine strain derived from *M. bovis,* in order to confirm the identity of the putative *M. tuberculosis pncA* gene. Indeed, the cosmid DNA containing the putative *M. tuberculosis pncA* gene conferred PZase activity to BCG, a natural mutant defective in PZase. The integration of the pncA cosmid DNA into *M. bovis* BCG genome was confirmed by Southern analysis. The functional *M. tuberculosis pncA* gene was localized on a 3.2 kb EcoRI-PstI fragment (FIG. 3A), by restriction mapping of the cosmid DNA in combination with BCG transformation studies using DNA constructs derived from the cosmid DNA insert. To confirm that the PZase activity is due to the pncA gene, but not to other DNA in the pncA upstream region on the 3.2 kb EcoRI-PstI fragment, BCG was transformed with the 2.3 kb EcoRI-SmaI DNA construct that contains the pncA upstream region and partial pncA gene; however, no PZase activity was detectable in the BCG transformant. Sequence analysis of the 2.3 kb EcoRI-SmaI fragment does not show significant open reading frames with homology to other known proteins in the database. Transformation of BCG with a construct that contains the pncA gene alone with its 120 bp upstream sequence as a PCR fragment gave functional expression of PZase activity, indicating that the PZase activity was indeed conferred by the pncA gene.

Sequence analysis revealed that the *M. tuberculosis pncA* gene (558 bp) encoded a protein of 186 amino acids (FIG. 1), with 35.5% overall amino acid identity to the *E. coli* nicotinamidase (Jerlstrom, et al., Gene 78, 37–46 (1989)) (FIG. 3B). The predicted molecular mass of the *M. tuberculosis* PZase is approximately 20 kilodaltons (kD), and is smaller than the *E. coli* homolog which consists of 213 amino acids with a size of 23 kD (Jerlstrom, et al., Gene 78, 37–46 (1989)).

Identification of mutations in the pncA gene of PZA-resistant strains. Using the 3.2 kb EcoRI-PstI pncA containing DNA fragment as a probe, Southern blotting analysis was performed on a panel of 8 PZA-resistant *M. tuberculosis* strains, 3 *M. bovis* strains and 3 BCG substrains. None of these strains had any gross deletions of the pncA gene or restriction fragment length polymorphism. *M. bovis,* as a species, lacks PZase (Konno, et al., Nature, 184, 1743–1744 (1959)) (Konno, et al., Am Rev. Respir. Dis. 95, 461–469 (1967), yet it nonetheless had the pncA gene, as evidenced by the same sized hybridization fragment as that in *M. tuberculosis.* The *M. tuberculosis pncA* gene did not hybridize with genomic DNA from mycobacterial species that do not cause respiratory tuberculosis, such as *M. smegmatis, M. vaccae* and *M. kansasii.*

The sequence of the pncA gene from naturally PZA-resistant *M. bovis* and an a panel of acquired PZA-resistant *M. tuberculosis* strains was determined. Surprisingly, three *M. bovis* strains (Ravenel, and two veterinary isolates) and three BCG substrains (Pasteur, Copenhagen, Glaxo) all had the same single point mutation in the pncA gene, changing from "C" to "G" at nucleotide position 169, which caused a substitution of Histidine (CAC) for Aspartic Acid (GAC) at amino acid position 57 of the PZase polypeptide (FIG. 1). Because no other mutations were found in the pncA gene, this particular substitution is concluded to have caused the defective PZase in these *M. bovis* and BCG strains. Consistent with this conclusion is the observation that, the BCG strains transformed with the 3.2 kb EcoRI-PstI construct containing the functional *M. tuberculosis* pncA gene restored PZase sensitivity.

Of the 8 sequenced *M. tuberculosis* strains that are PZA-resistant in conventional tests, 5 strains had point mutations within the pncA gene (see Table 1 above). The H37Rv, CSU20, and CSU25 strains lacked mutations in the pncA gene. The PZA-resistant strain PZA-R (ATCC 35828, PZase-negative) derived from H37Rv, and one MDR strain "Vertullo" each had a single nucleotide "G" missing at nucleotide positions 288 and 162, respectively, leading to premature termination that caused truncated polypeptides with no PZase activity. Three other PZA-resistant clinical isolates of *M. tuberculosis* (MDR strains) contained missense mutations in the pncA gene, causing substitutions at the following amino acid positions: Asp63 (GAC)→His (<u>C</u>AC), Cysl38 (TGT)→Ser (<u>A</u>GT), Glnl41 (CAG)→Pro (C<u>C</u>G). These data suggest that these substitutions are responsible for PZA-resistance and the defective PZase enzyme activity in these PZA-resistant strains. Of the 3 apparently PZA-resistant strains (CSU20, CSU25, and H7728) that did not have mutations in the pncA gene, re-testing of the minimal inhibitory concentration (MIC) of PZA indicated that these three strains are "false resistant," and are in fact susceptible to PZA with positive PZase activity.

Use of PCR-SSCP to distinguish *M. bovis* from *M. tuberculosis.* In this example, PCR was performed using the following cycling parameters: 95° C. for 5 minutes, followed by 30 cycles of (95° C. for 1 minute, 55° C. for 1 minute, and 72° C. for 1 minute). The PCR reaction included 1 X PCR Buffer (GIBCO BRL), dNTPs at 100$\mu$ mole, primers at 0.1 $\mu$g, mycobacterial genomic DNA 0.1–0.5 $\mu$g (V. P. Shankar; Texas A & M University Health Science Center), and 2.5 units of Taq DNA polymerase (GIBCO BRL). The primers used for detection of *M. bovis* were:

5'-GATTGCCGACGTGTCCAGAC-3' (SEQ ID NO: 3) and

5'-ATCAGCGACTACCTGGCCGA-3' (SEQ ID NO: 4), corresponding to nucleotides 91–110 and 270–251, respectively, of the pncA gene. When used together, these primers amplify a 180 bp DNA fragment.

Polyacrylamide gel electrophoresis was used to show the single strand conformation polymorphism in the amplified DNA. The PCR products (10 $\mu$l, containing 0.5–1.0 $\mu$g DNA) were denatured by boiling for 5–10 minutes in formamide dye. The boiled DNA was immediately incubated on ice for 5–10 minutes. The denatured DNA then was electrophoresed on a 20% polyacrylamide/5% glycerol gel (16×20 cm) that was pre-cooled to 4° C. The gel was electrophoresed in 0.5 X TBE buffer at a constant power of 5 W at 4° C. overnight. The gel then was stained with ethidium bromide (0.5 $\mu$g/ml), and the SSCP bands were visualized under UV light. As is illustrated in FIG. 4, the mobility of DNA corresponding to *M. bovis* differs from the mobility of DNA corresponding to *M. tuberculosis.* Thus, *M. bovis* strains can be rapidly differentiated from *M. tuberculosis* by PCR-SSCP, based on the detection of a characteristic *M. bovis* alteration in the pncA gene.

Use of PCR-SSCP to Identify PZA-resistant Strains of *M. tuberculosis.* In this example, PCR-SSCP was performed essentially as described above, except that the primers and mycobacterial DNA differed. The primers used were:

P3: 5'-CGTCGACGTGCAGAACGACT-3' (SEQ ID NO: 7);

P4: 5'-GATTGCCGACGTGTCCAGAC-3' (SEQ ID NO: 8);

P5: 5'-ACCGGACTATTCCTCGTCGT-3' (SEQ ID NO: 9);

P6: 5'-GCGCACACAATGATCGGTGG-3' (SEQ ID NO: 10);

P7: 5'-GCGGCTTCGAAGGAGTCGAC-3' (SEQ ID NO: 11); and

P8: 5'-GCTTTGCGGCGAGCGCTCCA-3' (SEQ ID NO: 12).

By using these primers in pairs (P3 with P4; P5 with P6; and P7 with P8), overlapping portions (~200 bp) of the pncA gene are amplified, which together correspond to nearly the entire pncA gene (FIG. 2). By using a set of primers that amplify several portions of the pncA, one can use PCR-SSCP to identify a PZA-resistant mycobacterium, even if one does not know precisely where in the pncA gene an alteration is located.

As was the case for *M. bovis* above, polyacrylamide gel electrophoresis was used to show the single strand conformation polymorphism in the amplified DNA after the DNA was denatured and cooled on ice. As is illustrated in FIG. 5, the mobility of DNA corresponding to PZA-resistant *M. tuberculosis* differs from the mobility of DNA corresponding to wild-type (PZA-sensitive) *M. tuberculosis*. Thus, PZA-resistant strains of *M. tuberculosis* can be rapidly identified by PCR-SSCP.

Transformation of PZA-resistant strains with a functional pncA gene. As is shown below, introduction of a functional pncA gene into a PZA-resistant *M. bovis* or *M. tuberculosis* renders the mycobacterium PZA-sensitive. In this case, the susceptibility of *M. bovis* BCG and the *M. tuberculosis* strain PZA-R were tested. The *M. bovis* BCG is a naturally PZA-resistant strain, and the *M. tuberculosis* strain PZA-R is an acquired resistance strain derived from H37Rv. These two PZA-resistant strains were transformed with the 3.2 kb EcoRI-PstI plasmid construct that contains the functional pncA gene. In both cases, the resulting pncA transformants expressed PZase enzyme activity and became susceptible to PZA (MIC=50 μg ml$^{-1}$) at acid pH (5.5) in vitro. In contrast, BCG and PZA-R vector control strains remained PZA-resistant (MIC>1000 μg ml$^{-}$) and PZase-negative.

The pncA gene can also be used to render intracellular *M. tuberculosis* susceptible to PZA. In this case, the recombinant *M. bovis* was tested for PZA-susceptibility while inside macrophages. Indeed, the recombinant BCG expressing the *M. tuberculosis* PZase became susceptible to PZA in J774 macrophages. By contrast, the control BCG remained resistant to PZA at various drug concentrations (Table 2). At high PZA concentrations (500 μg ml$^{-1}$), the control BCG was also inhibited slightly, but not as much as the recombinant BCG. In a parallel control experiment with streptomycin, both the recombinant BCG and the vector control BCG were equally inhibited by streptomycin in J774 macrophages (Table 2), indicating that the PZA susceptibility of the recombinant BCG is due to expression of the PZase activity conferred by the *M. tuberculosis* pncA gene.

TABLE 2

PZA Susceptibility of Recombinant BCG in J774 Macrophage

| Drugs | Drug concentration (μg/ml) | Number of bacilli per macrophage BCG recombinant (PZase$^+$) | BCG vector (PZase$^-$) |
|---|---|---|---|
| PZA | 0 | >20 | >20 |
|  | 25 | 7 | >20 |
|  | 200 | 5 | 15 |
|  | 500 | 2 | 15 |
| Streptomycin | 0 | >20 | >20 |
|  | 25 | 8 | 9 |
|  | 50 | 4 | 7 |
|  | 100 | 4 | 4 |

Although the invention has been described with reference to the presently preferred embodiment, it should be understood that various modifications can be made without departing from the spirit of the invention. Accordingly, the invention is limited only by the following claims.

What is claimed is:

1. An isolated nucleic acid encoding an *M. tuberculosis* pyrazinamidase (PZase) polypeptide having the amino acid sequence of SEQ. ID NO: 2 or a fragment thereof having biological activity of SEQ. ID No. 2.

2. The nucleic acid of claim 1, wherein the nucleic acid has the sequence of FIG. 1 (SEQ ID NO: 1), or degenerate variants thereof, and encodes the amino acid sequence of FIG. 1 (SEQ ID NO: 2).

3. An isolated nucleic acid encoding a conservative variation of SEQ. ID NO: 2 and having a biological activity of SEQ. ID NO: 2.

4. An isolated nucleic acid encoding an altered *M. tuberculosis* PZase polypeptide having the sequence of SEQ. ID NO: 2, except for a −1 frameshift at amino acid position 96.

5. The nucleic acid of claim 4, wherein the nucleic acid comprises a deletion of nucleotide 288 of SEQ. ID NO: 1.

6. An isolated nucleic acid encoding an altered *M. tuberculosis* PZase polypeptide having the amino acid sequence of SEQ ID NO: 2 except for a −1 frameshift at amino acid position.

7. The nucleic acid of claim 6, wherein the nucleic acid comprises a deletion of nucleotide 162 of SEQ. ID NO: 1.

8. An isolated nucleic acid encoding an altered *M. tuberculosis* PZase polypeptide having the amino acid sequence of SEQ. ID NO: 2, except for a histidine residue at amino acid position.

9. The nucleic acid of claim 8, wherein the nucleic acid comprises a change of G to C at nucleotide 187 of SEQ. ID NO: 1.

10. An isolated nucleic acid encoding an altered *M. tuberculosis* PZase polypeptide, wherein the nucleic acid encodes a serine residue at amino acid position 138 of SEQ. ID NO: 2.

11. The nucleic acid of claim 10, wherein the nucleic acid comprises a change of T to A at nucleotide 412 of SEQ. ID NO: 1.

12. An isolated nucleic acid encoding an altered *M. tuberculosis* PZase polypeptide, wherein the nucleic acid encodes a polypeptide having the sequence of SEQ. ID. NO: 2, except for a proline residue at amino acid position 141.

13. The nucleic acid of claim 12, wherein the nucleic acid comprises a change of A to C at nucleotide 422 of SEQ. ID NO: 1.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 561 base pairs
( B ) TYPE: nucleic acid
( C ) STRANDEDNESS: single
( D ) TOPOLOGY: linear ( i x ) FEATURE:
( A ) NAME/KEY: CDS
( B ) LOCATION: 1..561

( x i ) SEQUENCE DESCRIPTION: SEQ ID NO:1:

```
ATG  CGG  GCG  TTG  ATC  ATC  GTC  GAC  GTG  CAG  AAC  GAC  TTC  TGC  GAG  GGT        48
Met  Arg  Ala  Leu  Ile  Ile  Val  Asp  Val  Gln  Asn  Asp  Phe  Cys  Glu  Gly
 1                    5                       10                      15

GGC  TCG  CTG  GCG  GTA  ACC  GGC  GGC  GCC  GCG  CTG  GCC  CGC  GCC  ATC  AGC        96
Gly  Ser  Leu  Ala  Val  Thr  Gly  Gly  Ala  Ala  Leu  Ala  Arg  Ala  Ile  Ser
               20                       25                      30

GAC  TAC  CTG  GCC  GAA  GCG  GCG  GAC  TAC  CAT  CAC  GTC  GTG  GCA  ACC  AAG       144
Asp  Tyr  Leu  Ala  Glu  Ala  Ala  Asp  Tyr  His  His  Val  Val  Ala  Thr  Lys
               35                       40                      45

GAC  TTC  CAC  ATC  GAC  CCG  GGT  GAC  CAC  TTC  TCC  GGC  ACA  CCG  GAC  TAT       192
Asp  Phe  His  Ile  Asp  Pro  Gly  Asp  His  Phe  Ser  Gly  Thr  Pro  Asp  Tyr
          50                       55                      60

TCC  TCG  TCG  TGG  CCA  CCG  CAT  TGC  GTC  AGC  GGT  ACT  CCC  GGC  GCG  GAC       240
Ser  Ser  Ser  Trp  Pro  Pro  His  Cys  Val  Ser  Gly  Thr  Pro  Gly  Ala  Asp
 65                      70                       75                      80

TTC  CAT  CCC  AGT  CTG  GAC  ACG  TCG  GCA  ATC  GAG  GCG  GTG  TTC  TAC  AAG       288
Phe  His  Pro  Ser  Leu  Asp  Thr  Ser  Ala  Ile  Glu  Ala  Val  Phe  Tyr  Lys
```

|     |     |     |     |     |     |     |     |     |     |     |     |     |     |     |     |     |
|-----|-----|-----|-----|-----|-----|-----|-----|-----|-----|-----|-----|-----|-----|-----|-----|-----|
|     |     |     |     | 85  |     |     |     |     | 90  |     |     |     |     | 95  |     |     |
| GGT | GCC | TAC | ACC | GGA | GCG | TAC | AGC | GGC | TTC | GAA | GGA | GTC | GAC | GAG | AAC | 336 |
| Gly | Ala | Tyr | Thr | Gly | Ala | Tyr | Ser | Gly | Phe | Glu | Gly | Val | Asp | Glu | Asn |     |
|     |     |     | 100 |     |     |     |     | 105 |     |     |     | 110 |     |     |     |     |
| GGC | ACG | CCA | CTG | CTG | AAT | TGG | CTG | CGG | CAA | CGC | GGC | GTC | GAT | GAG | GTC | 384 |
| Gly | Thr | Pro | Leu | Leu | Asn | Trp | Leu | Arg | Gln | Arg | Gly | Val | Asp | Glu | Val |     |
|     |     | 115 |     |     |     |     | 120 |     |     |     |     | 125 |     |     |     |     |
| GAT | GTG | GTC | GGT | ATT | GCC | ACC | GAT | CAT | TGT | GTG | CGC | CAG | ACG | GCC | GAG | 432 |
| Asp | Val | Val | Gly | Ile | Ala | Thr | Asp | His | Cys | Val | Arg | Gln | Thr | Ala | Glu |     |
|     | 130 |     |     |     |     | 135 |     |     |     |     | 140 |     |     |     |     |     |
| GAC | GCG | GTA | CGC | AAT | GGC | TTG | GCC | ACC | AGG | GTG | CTG | GTG | GAC | CTG | ACA | 480 |
| Asp | Ala | Val | Arg | Asn | Gly | Leu | Ala | Thr | Arg | Val | Leu | Val | Asp | Leu | Thr |     |
| 145 |     |     |     |     | 150 |     |     |     |     | 155 |     |     |     |     | 160 |     |
| GCG | GGT | GTG | TCG | GCC | CAT | ACC | ACC | GTC | GCC | GCG | CTG | GAG | GAG | ATG | CGC | 528 |
| Ala | Gly | Val | Ser | Ala | His | Thr | Thr | Val | Ala | Ala | Leu | Glu | Glu | Met | Arg |     |
|     |     |     |     | 165 |     |     |     |     | 170 |     |     |     |     | 175 |     |     |
| ACC | GCC | AGC | GTC | GAG | TTG | GTT | TGC | AGC | TCC | TGA |     |     |     |     |     | 561 |
| Thr | Ala | Ser | Val | Glu | Leu | Val | Cys | Ser | Ser | *   |     |     |     |     |     |     |
|     |     |     | 180 |     |     |     |     | 185 |     |     |     |     |     |     |     |     |

( 2 ) INFORMATION FOR SEQ ID NO:2:

( i ) SEQUENCE CHARACTERISTICS:
        ( A ) LENGTH: 186 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

| Met | Arg | Ala | Leu | Ile | Ile | Val | Asp | Val | Gln | Asn | Asp | Phe | Cys | Glu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gly | Ser | Leu | Ala | Val | Thr | Gly | Gly | Ala | Ala | Leu | Ala | Arg | Ala | Ile | Ser |
|     |     |     |     | 20  |     |     |     |     | 25  |     |     |     |     | 30  |     |
| Asp | Tyr | Leu | Ala | Glu | Ala | Ala | Asp | Tyr | His | His | Val | Val | Ala | Thr | Lys |
|     |     |     | 35  |     |     |     |     | 40  |     |     |     |     | 45  |     |     |
| Asp | Phe | His | Ile | Asp | Pro | Gly | Asp | His | Phe | Ser | Gly | Thr | Pro | Asp | Tyr |
|     |     | 50  |     |     |     |     | 55  |     |     |     |     | 60  |     |     |     |
| Ser | Ser | Ser | Trp | Pro | Pro | His | Cys | Val | Ser | Gly | Thr | Pro | Gly | Ala | Asp |
| 65  |     |     |     |     | 70  |     |     |     |     | 75  |     |     |     |     | 80  |
| Phe | His | Pro | Ser | Leu | Asp | Thr | Ser | Ala | Ile | Glu | Ala | Val | Phe | Tyr | Lys |
|     |     |     |     | 85  |     |     |     |     | 90  |     |     |     |     | 95  |     |
| Gly | Ala | Tyr | Thr | Gly | Ala | Tyr | Ser | Gly | Phe | Glu | Gly | Val | Asp | Glu | Asn |
|     |     |     | 100 |     |     |     |     | 105 |     |     |     |     | 110 |     |     |
| Gly | Thr | Pro | Leu | Leu | Asn | Trp | Leu | Arg | Gln | Arg | Gly | Val | Asp | Glu | Val |
|     |     | 115 |     |     |     |     | 120 |     |     |     |     | 125 |     |     |     |
| Asp | Val | Val | Gly | Ile | Ala | Thr | Asp | His | Cys | Val | Arg | Gln | Thr | Ala | Glu |
|     | 130 |     |     |     |     | 135 |     |     |     |     | 140 |     |     |     |     |
| Asp | Ala | Val | Arg | Asn | Gly | Leu | Ala | Thr | Arg | Val | Leu | Val | Asp | Leu | Thr |
| 145 |     |     |     |     | 150 |     |     |     |     | 155 |     |     |     |     | 160 |
| Ala | Gly | Val | Ser | Ala | His | Thr | Thr | Val | Ala | Ala | Leu | Glu | Glu | Met | Arg |
|     |     |     |     | 165 |     |     |     |     | 170 |     |     |     |     | 175 |     |
| Thr | Ala | Ser | Val | Glu | Leu | Val | Cys | Ser | Ser |     |     |     |     |     |     |
|     |     |     | 180 |     |     |     |     | 185 |     |     |     |     |     |     |     |

( 2 ) INFORMATION FOR SEQ ID NO:3:

( i ) SEQUENCE CHARACTERISTICS:
        ( A ) LENGTH: 20 base pairs
        ( B ) TYPE: nucleic acid ( C ) STRANDEDNESS: single
( D ) TOPOLOGY: linear ( x i ) SEQUENCE DESCRIPTION: SEQ ID NO:3:

GATTGCCGAC GTGTCCAGAC                      20

( 2 ) INFORMATION FOR SEQ ID NO:4:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear    ( x i ) SEQUENCE DESCRIPTION: SEQ ID NO:4:

ATCAGCGACT ACCTGGCCGA                      20

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear    ( x i ) SEQUENCE DESCRIPTION: SEQ ID NO:5:

GCTGGTCATG TTCGCGATCG                      20

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear    ( x i ) SEQUENCE DESCRIPTION: SEQ ID NO:6:

TCGGCCAGGT AGTCGCTGAT                      20

( 2 ) INFORMATION FOR SEQ ID NO:7:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear    ( x i ) SEQUENCE DESCRIPTION: SEQ ID NO:7:

CGTCGACGTG CAGAACGACT                      20

( 2 ) INFORMATION FOR SEQ ID NO:8:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear    ( x i ) SEQUENCE DESCRIPTION: SEQ ID NO:8:

GATTGCCGAC GTGTCCAGAC                      20

( 2 ) INFORMATION FOR SEQ ID NO:9:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:9:

ACCGGACTAT TCCTCGTCGT 20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

GCGCACACAA TGATCGGTGG 20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

GCGGCTTCGA AGGAGTCGAC 20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

GCTTTGCGGC GAGCGCTCCA 20

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: linear     ( i i ) MOLECULE TYPE: protein     ( x i ) SEQUENCE DESCRIPTION: SEQ ID NO:13:

Val Asp Leu Gln Asn Asp Phe Cys Ala
    1                    5

( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: Not Relevant
        ( D ) TOPOLOGY: linear     ( i i ) MOLECULE TYPE: protein     ( x i ) SEQUENCE DESCRIPTION: SEQ ID NO:14:

Gly Tyr Lys Val Asn Val Ile Thr Asp Gly Cys
    1                    5                        10

( 2 ) INFORMATION FOR SEQ ID NO:15:

( i ) SEQUENCE CHARACTERISTICS:

(A) LENGTH: 186 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:15:

```
Met Arg Ala Leu Ile Ile Val Asp Val Gln Asn Asp Phe Cys Glu Gly
1               5                   10                  15

Gly Ser Leu Ala Val Thr Gly Gly Ala Ala Leu Ala Arg Ala Ile Ser
                20                  25                  30

Asp Tyr Leu Ala Glu Ala Ala Asp Tyr His His Val Val Ala Thr Lys
                35                  40                  45

Asp Phe His Ile Asp Pro Gly Asp His Phe Ser Gly Thr Pro Asp Tyr
        50                  55                  60

Ser Ser Ser Trp Pro Pro His Cys Val Ser Gly Thr Pro Gly Ala Asp
65                  70                  75                  80

Phe His Pro Ser Leu Asp Thr Ser Ala Ile Glu Ala Val Phe Tyr Lys
                85                  90                  95

Gly Ala Tyr Thr Gly Ala Tyr Ser Gly Phe Glu Gly Val Asp Glu Asn
                100                 105                 110

Gly Thr Pro Leu Leu Asn Trp Leu Arg Gln Arg Gly Val Asp Glu Val
            115                 120                 125

Asp Val Val Gly Ile Ala Thr Asp His Cys Val Arg Gln Thr Ala Glu
    130                 135                 140

Asp Ala Val Arg Asn Gly Leu Ala Thr Arg Val Leu Val Asp Leu Thr
145                 150                 155                 160

Ala Gly Val Ser Ala Asp Ile Thr Val Ala Ala Leu Glu Glu Met Arg
                    165                 170                 175

Thr Ala Ser Val Glu Leu Val Cys Ser Ser
                180                 185
```

(2) INFORMATION FOR SEQ ID NO:16:

(i) SEQUENCE CHARACTERISTICS:
(A) LENGTH: 213 amino acids
(B) TYPE: amino acid
(C) STRANDEDNESS: Not Relevant
(D) TOPOLOGY: linear (ii) MOLECULE TYPE: protein (xi) SEQUENCE DESCRIPTION: SEQ ID NO:16:

```
Met Pro Pro Arg Ala Leu Leu Leu Val Asp Leu Gln Asn Asp Phe Cys
1               5                   10                  15

Ala Gly Gly Ala Leu Ala Val Pro Glu Gly Asp Ser Thr Val Asp Val
                20                  25                  30

Ala Asn Arg Leu Ile Asp Trp Cys Gln Ser Arg Gly Glu Ala Val Ile
            35                  40                  45

Ala Ser Gln Asp Trp His Pro Ala Asn His Gly Ser Phe Ala Ser Gln
        50                  55                  60

His Gly Val Glu Pro Tyr Thr Pro Gly Gln Leu Asp Gly Leu Pro Gln
65                  70                  75                  80

Thr Phe Trp Pro Asp His Cys Val Gln Asn Ser Glu Gly Ala Gln Leu
                85                  90                  95

His Pro Leu Leu His Gln Lys Ala Ile Ala Ala Val Phe His Lys Gly
            100                 105                 110

Glu Asn Pro Leu Val Asp Ser Tyr Ser Ala Phe Phe Asp Asn Gly Arg
```

|     |     |     |     |     |     | 115 |     |     |     |     |     |     | 120 |     |     |     |     |     |     | 125 |     |     |     |
| --- | --- | --- | --- | --- | --- | --- | --- | --- | --- | --- | --- | --- | --- | --- | --- | --- | --- | --- | --- | --- | --- | --- | --- |
| Arg | Gln 130 | Lys | Thr | Ser | Leu | Asp 135 | Asp | Trp | Leu | Arg | Asp 140 | His | Glu | Ile | Asp |
| Glu 145 | Leu | Ile | Val | Met | Gly 150 | Leu | Ala | Thr | Asp | Tyr 155 | Cys | Val | Lys | Phe | Thr 160 |
| Val | Leu | Asp | Ala | Leu 165 | Gln | Leu | Gly | Tyr | Lys 170 | Val | Asn | Val | Ile | Thr 175 | Asp |
| Gly | Cys | Arg | Gly 180 | Val | Asn | Ile | Gln | Pro 185 | Gln | Asp | Ser | Ala | His 190 | Ala | Phe |
| Met | Glu | Met 195 | Ser | Ala | Ala | Gly | Ala 200 | Thr | Leu | Tyr | Thr | Leu 205 | Ala | Asp | Trp |
| Glu | Glu 210 | Thr | Gln | Gly |